US008588511B2

(12) United States Patent
Liu et al.

(10) Patent No.: US 8,588,511 B2
(45) Date of Patent: Nov. 19, 2013

(54) METHOD AND APPARATUS FOR AUTOMATIC MEASUREMENT OF PAD GEOMETRY AND INSPECTION THEREOF

(75) Inventors: Gang Liu, Framingham, MA (US); Aaron S. Wallack, Natick, MA (US); David J. Michael, Wayland, MA (US)

(73) Assignee: Cognex Corporation, Natick, MA (US)

( * ) Notice: Subject to any disclaimer, the term of this patent is extended or adjusted under 35 U.S.C. 154(b) by 902 days.

(21) Appl. No.: 11/613,087

(22) Filed: Dec. 19, 2006

(65) Prior Publication Data

US 2008/0144917 A1 Jun. 19, 2008

Related U.S. Application Data

(63) Continuation of application No. 10/389,475, filed on Mar. 14, 2003, now Pat. No. 7,171,036.

(60) Provisional application No. 60/382,896, filed on May 22, 2002, provisional application No. 60/432,054, filed on Dec. 10, 2002.

(51) Int. Cl.
*G06K 9/00* (2006.01)
*G06K 9/48* (2006.01)
*H04N 7/18* (2006.01)

(52) U.S. Cl.
USPC .......... 382/147; 382/149; 382/199; 382/151; 348/125

(58) Field of Classification Search
USPC .......... 382/141, 147, 199, 151, 149; 348/125
See application file for complete search history.

(56) References Cited

U.S. PATENT DOCUMENTS

| | | | | |
|---|---|---|---|---|
| 4,651,341 A | * | 3/1987 | Nakashima et al. | 382/222 |
| 4,799,268 A | * | 1/1989 | McLean et al. | 382/146 |
| 4,830,497 A | * | 5/1989 | Iwata et al. | 356/394 |
| 4,893,346 A | * | 1/1990 | Bishop | 382/147 |
| 5,093,797 A | * | 3/1992 | Yotsuya et al. | 716/119 |
| 5,134,575 A | * | 7/1992 | Takagi | 382/147 |
| 5,134,665 A | * | 7/1992 | Jyoko | 382/150 |
| 5,150,422 A | * | 9/1992 | Kitakado et al. | 382/148 |
| 5,214,712 A | * | 5/1993 | Yamamoto et al. | 382/149 |
| 5,301,248 A | * | 4/1994 | Takanori et al. | 382/147 |
| 5,398,291 A | * | 3/1995 | Kitakado et al. | 382/145 |
| 5,408,538 A | * | 4/1995 | Kitakado et al. | 382/145 |
| 5,978,521 A | | 11/1999 | Wallack et al. | |
| 6,078,700 A | | 6/2000 | Sarachik | |
| 6,256,398 B1 | * | 7/2001 | Chang | 382/100 |
| 6,459,807 B1 | * | 10/2002 | Guest et al. | 382/145 |
| 6,813,377 B1 | * | 11/2004 | Gopalakrishnan et al. | 382/146 |
| 6,823,044 B2 | * | 11/2004 | Rosner | 378/98.8 |
| 6,950,548 B1 | * | 9/2005 | Bachelder et al. | 382/145 |
| 6,987,875 B1 | * | 1/2006 | Wallack | 382/146 |
| 7,242,080 B2 | * | 7/2007 | Matsuno | 257/679 |
| 7,315,642 B2 | * | 1/2008 | Bartov | 382/145 |
| 7,336,816 B2 | * | 2/2008 | Sasazawa et al. | 382/150 |
| 7,381,066 B2 | * | 6/2008 | Higashiguchi et al. | 439/83 |
| 7,639,860 B2 | * | 12/2009 | Sasai | 382/141 |
| 2001/0051394 A1 | * | 12/2001 | Kim et al. | 438/106 |
| 2002/0191832 A1 | * | 12/2002 | Guest et al. | 382/145 |
| 2003/0223631 A1 | * | 12/2003 | Ine | 382/145 |
| 2006/0023936 A1 | * | 2/2006 | Fujiwara | 382/149 |
| 2006/0181299 A1 | * | 8/2006 | Hirae | 324/765 |
| 2006/0245637 A1 | * | 11/2006 | Prince | 382/150 |
| 2007/0147676 A1 | * | 6/2007 | Sasai | 382/149 |

\* cited by examiner

*Primary Examiner* — Kathleen Y Dulaney
(74) *Attorney, Agent, or Firm* — Loginov & Associates, PLLC

(57) ABSTRACT

An image of a semiconductor interconnection pad is analyzed to determine a geometric description of the zone regions of a multiple zone semiconductor interconnection pad. Edge detection machine vision tools are used to extract features in the image. The extracted features are analyzed to derive geometric descriptions of the zone regions of the pad, that are applied in semiconductor device inspection, fabrication, and assembly operations.

14 Claims, 5 Drawing Sheets

METHOD AND APPARATUS FOR AUTOMATIC MEASUREMENT OF PAD GEOMETRY AND INSPECTION THEREOF

CROSS REFERENCE TO RELATED APPLICATIONS

This application is a continuation of U.S. patent application Ser. No. 10/389,475, filed Mar. 14, 2003, entitled "Method and Apparatus for Automatic Measurement of Pad Geometry and Inspection thereof", which claims the benefit of priority of Provisional U.S. Patent Application Ser. No. 60/382,896, filed May 22, 2002, entitled "Image Processing for Probe Mark Inspection," and Provisional U.S. Patent Application Ser. No. 60/432,054, entitled "Automatic Measurement of Pad Geometry in Probe Mark Inspection", filed Dec. 10, 2002.

BACKGROUND OF THE INVENTION

The present invention relates to the application of machine vision algorithms in the manufacture of semiconductor devices. Specifically, the invention applies to automatic detection and analysis of geometric patterns on the surface of interconnection lands, or pads, of integrated circuits, or semiconductor devices. Semiconductor devices are more recently being designed and fabricated with pads having multiple regions or zones that appear as a series of concentric geometric patterns. Automatic detection and analysis of multiple zones of pads of semiconductor devices is useful in various methods of semiconductor device fabrication, including, for example, in a probe mark inspection operation. A probe mark inspection operation is typically performed subsequent to an electrical testing operation of the semiconductor device, to ascertain that mechanical probe marks exist, indicating that an electrical test has been performed. The use of an apparatus that can automatically detect and analyze probe marks on device lands can be more reliable and accurate than manual inspection with the human eye.

Silicon device fabrication involves various circuit definition steps with chemical processing of a wafer containing an array of multiple devices. An electrical test of the wafer is typically employed to identify defective devices and/or to perform process control. The electrical test is performed by probing the wafer with needle-tipped probes, leaving an indentation or surface finish aberration on the pad where the probe made contact with the pad. An inspection of the mark left by the electrical testing probe may be performed subsequent to the electrical test to visually assess the electrical testing operations. Absence of a mark, or misalignment of the mark on the pad, would indicate that the test was not properly performed. Additionally, data collected from a probe mark inspection may be useful in process characterization and process control of equipment alignment parameters.

Probe mark inspection, as described in the commonly assigned U.S. patent application Ser. No. 10/032,168, entitled "Probe Mark Inspection Method and Apparatus," filed Dec. 21, 2001, incorporated by reference herein, is a useful operation in silicon device fabrication because of the increasing size, density, and value of the silicon wafers. Good devices must not be falsely identified as defective, whereas defective devices must be accurately identified so that needless processing and packaging effort is not further expended. Verification of the integrity of the electrical testing operation ensures that the devices are properly tested to avoid the cost penalties of false or improper indictment. Further, human visual inspection using a microscope is not only extremely tedious, but human operators performing inspection can actually introduce particulate contamination in a cleanroom environment that may impair processing yield. Thus, the operation is ideally suited for a computer-assisted machine vision application.

Probe mark inspection of semiconductor device pads having multiple zones may be performed differently for different zones of the pad. The inspection operation could be performed on the entire pad by ignoring the multiple zones, or restricted to only one zone or region comprising a portion of the pad, with reliable and useful results. The dimensions and position of the various pad zones is therefore a useful input to the inspection.

Currently, the various multiple zones or regions of a semiconductor device pad can be manually specified by an operator of an inspection apparatus. Geometric pattern matching tools, such as PATMAX® from Cognex Corporation, can be used to register, detect, and/or analyze zone boundaries of multiple zone pads, but such tools can be ineffective if the actual pad has more zones than the trained model. Additionally, the geometric pattern matching tools are typically not reliable due to extremely weak zone boundaries exhibited in a typical image of a pad.

For the foregoing reasons, there is a need for a machine vision apparatus that can automatically determine the geometry of multiple zones or regions of semiconductor device pads, in conjunction with a machine vision inspection operation to quickly and reliably assess the presence of a probe mark.

BRIEF SUMMARY OF THE INVENTION

The present invention is a method and system that automatically derives a geometric description of the zones of a multiple zone semiconductor device pad, for use in registration, inspection, fabrication, and assembly of such devices. More specifically, the invention is a method of inspecting a semiconductor interconnection pad using an acquired image of the pad. A geometric description of concentric multiple zone patterns on the pad is automatically derived from the image. This geometric description can then be used in the inspection of the pad from the image. Without having to manually specify or describe the multiple zone pad geometry, an inspection, such as, for example, probe mark inspection, can be performed using the geometric description of the multiple zone patterns on the pad.

A general object of the invention is to apply machine vision tools to the image to extract features, and generate hypothetical geometric descriptions using the features. The relationship of the grey level values of the pixels associated with the features can be analyzed to select the best hypothetical description to represent the geometric description of the multiple zone pattern on the pad.

An aspect of the invention is to inspect multiple zone semiconductor device pads for probe marks using the automatically-derived geometric description of the multiple zone pattern. Probe marks or other indicia may not be contained within a single zone, and conventional methods of inspecting a pad having multiple zones are not effective.

Another object of the invention is to provide an apparatus for inspecting an interconnection pad of a semiconductor device. A machine vision system can automatically derive a multiple zone geometric description of a pad having a multiple zone pattern. An image acquisition system, typically comprising a camera coupled to a framegrabber, is coupled to the machine vision system. The machine vision system can perform an inspection, such as, for example, probe mark inspection, using the geometric description of the multiple zone pattern on the pad.

The foregoing and other objects and advantages of the invention will appear from the following detailed description. In the description, reference is made to the accompanying drawings which form a part hereof, and in which there is shown by way of illustration an exemplary embodiment of the invention. Such embodiment does not necessarily represent the full scope of the invention, however, and reference is made therefore to the claims and herein for interpreting the scope of the invention.

BRIEF DESCRIPTION OF THE SEVERAL VIEWS OF THE DRAWING

The invention will be more fully understood from the following detailed description, in conjunction with the accompanying figures, wherein.

DETAILED DESCRIPTION OF THE INVENTION

Figure 1:
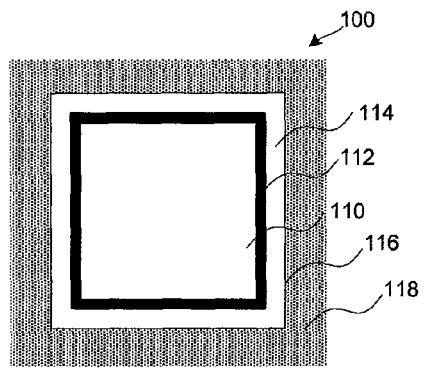
FIG. 1 is a depiction of a typical multiple zone interconnection pad of a semiconductor device.

Probe mark inspection is typically performed during silicon device fabrication to inspect for, and report characteristics of, the marks made on the surface of the silicon device interconnection pads by an electrical testing operation. Frequently, silicon device interconnection pads are fabricated such that geometric patterns appear on the surface of the pad. FIG. 1 depicts a silicon device interconnection pad with multiple zones that can be described by a geometric pattern. The pad 100 can have an inner zone 110, a distinct central zone 112, and an outer zone 114. The pad surface extends to the pad border 116, and the area surrounding the pad 100 is the device background 118. A probe mark inspection operation using machine vision must be capable of differentiating from the regions, or zones, defined by the geometric patterns, and the outer periphery of the pad surface.

To configure a probe mark inspection apparatus to distinguish between multiple zones on the surface of a pad 100, an operator can manually specify dimensions of the regions or zones, or semi-automatically using common machine vision pattern finding algorithms. A required input of either method is an a priori knowledge of the location and dimensions of the regions or zones defined by the geometric patterns.

Figure 2:
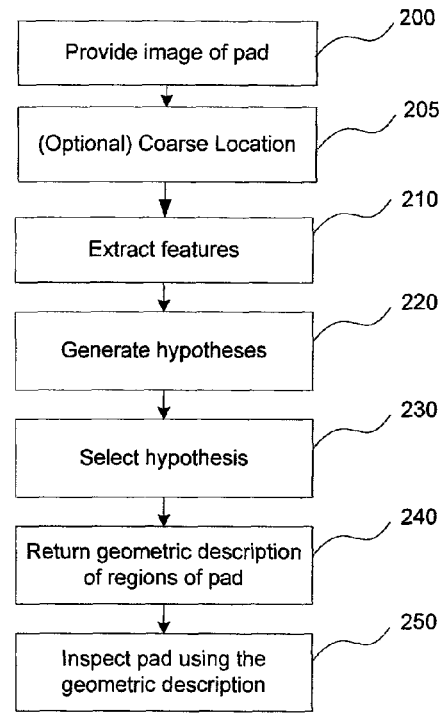
FIG. 2 is a flowchart of the general method of the present invention.

FIG. 2 is a flowchart of the present invention, to automatically derive geometric pattern characteristics from an image of the pad possibly without an a priori knowledge of the pattern characteristics. The main components of the method of the present invention, as described in FIG. 2, and further described hereinafter, comprise the steps of: providing an image of the pad 200; extracting features 210; generating hypotheses 220; selecting a hypothesis 230; returning a geometric description of regions of the pad 240 based on the hypothesis of step 230; and inspecting the pad 250 using the geometric description of regions of the pad from step 240.

Figure 3:
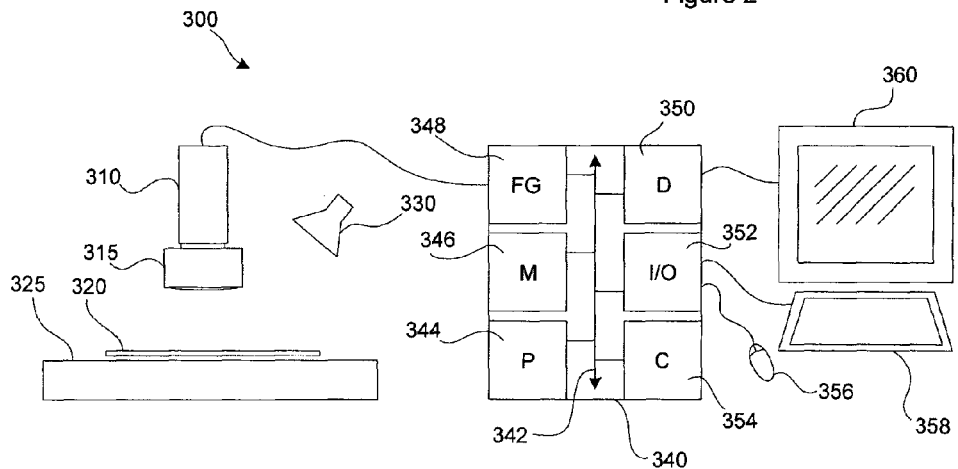
FIG. 3 is a diagram depicting the apparatus of the present invention.

The inspection of a probe mark on a semiconductor pad as generally described in FIG. 2 can be performed using an inspection apparatus 300 as shown in FIG. 3. The inspection apparatus 300 may include an image acquisition system comprising a camera 310 having a lens 315 cooperative to provide an image of the surface of a semiconductor wafer 320. The wafer 320 can be mounted on a translation table 325 to permit adjustment of the position of the wafer 320 relative to the camera 310. An illumination device 330 can be provided to sufficiently illuminate the surface of the wafer 320 for providing a quality image of the wafer 320.

The inspection apparatus 300 may include a machine vision system comprising a processor 344, a memory 346, a controller 354, a frame grabber 348, a display controller 350, an input/output (I/O) 352, and a communication data control bus 342 that couples elements 344-354 together and allows for cooperation and communication between those elements.

The camera 310 can be coupled to the frame grabber 348 for image acquisition by transferring images from the camera 310 to the general purpose computer 340 and the memory 346 therein.

The memory 346 may be preferably implemented with a sufficient quantity of random access memory (RAM), e.g., 128 megabytes, and hard disk storage, e.g., 10 gigabytes. A user can monitor the inspection apparatus 300 through the display controller 350, which can be coupled to a graphical display 360, and interact with the inspection apparatus 300 through the I/O 352, which can be coupled to a pointer device 356 and a keyboard 358.

The processor 344 works in cooperation with the controller 354 to control operation of the other elements 346-352. In cooperation with the controller 354, the processor 344 may fetch instructions from the memory 346 and decode them, which may cause the processor 344 to transfer data to or from memory 346 or work in combination with the frame grabber 348 and the display controller 350 to provide inspection information to the user via, for example, the display 360.

The controller 354 operates to control operation of the other elements 346-352 of the system 300. It should be appreciated that the controller 354 may be implemented with the processor 344, for example, in a central processing unit, or other similar device.

The inspection apparatus 300 can be implemented, for example, as portions of a suitably programmed general-purpose computer 340. The inspection apparatus 300 may alternatively be implemented, for example, as physically distinct hardware circuits within an ASIC device. The particular form of the inspection apparatus 300 can be different. For example, although the inspection apparatus 300 has been described to include a general-purpose computer 340, for example, a personal computer, it is foreseeable that the inspection apparatus 300 may include a special purpose embedded processor.

The inspection apparatus 300 can be configured to perform the method described in FIG. 2 to derive dimensions of the regions or zones in order to perform a probe mark inspection. To derive dimensions, or a geometric description of the regions or zones, the method of the present invention begins with an image of the pad in step 200. The image in the exemplary embodiment can have a resolution of 128×128 pixels at 8-bit greyscale depth. Optionally, as shown in FIG. 2, the user can specify a coarse pad size and location at step 205.

Figure 4:
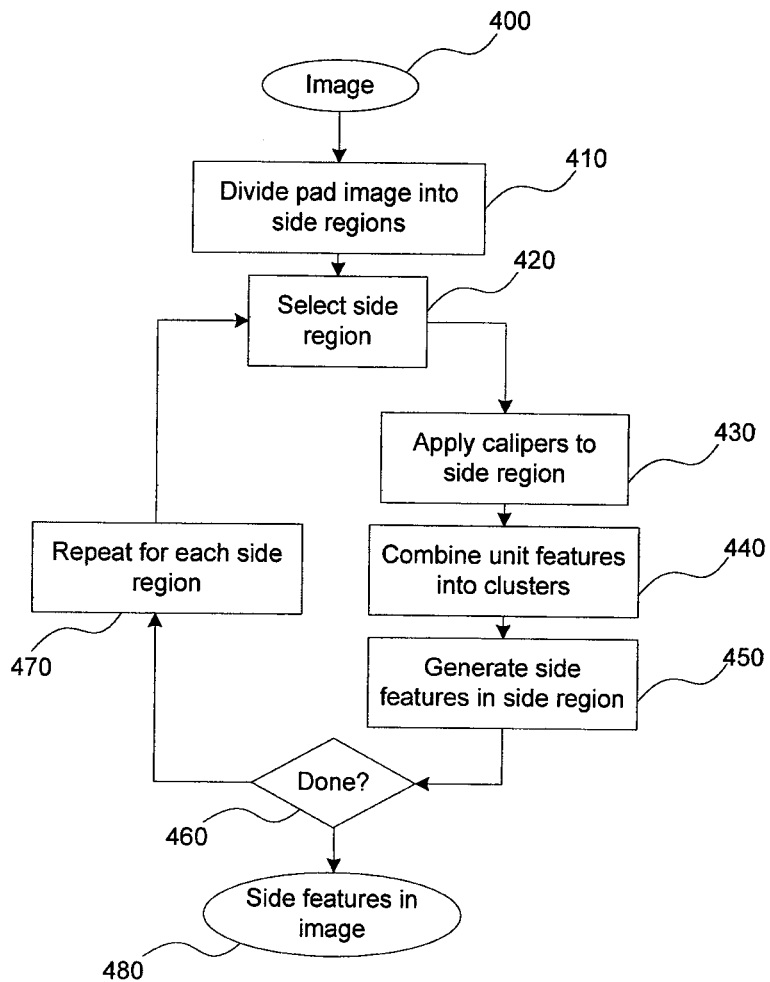
FIG. 4 is a flowchart of the method of extracting features from an image in an exemplary embodiment of the present invention.

Features are extracted from the image in step 210 of FIG. 2, as generally described in further detail in FIG. 4. The features extracted represent portions of the pad 100 that can be detected and arranged to represent a Geometric pattern describing the multiple zones of the pad 100. For example, features representing corner or side boundaries of the multiple zones of the pad 100 can be extracted. All possible features that could represent boundaries of the multiple zones of the pad are extracted, including features associated with noise, surface defects, probe marks, and features not associated with the boundaries of the multiple zones.

Figure 5:
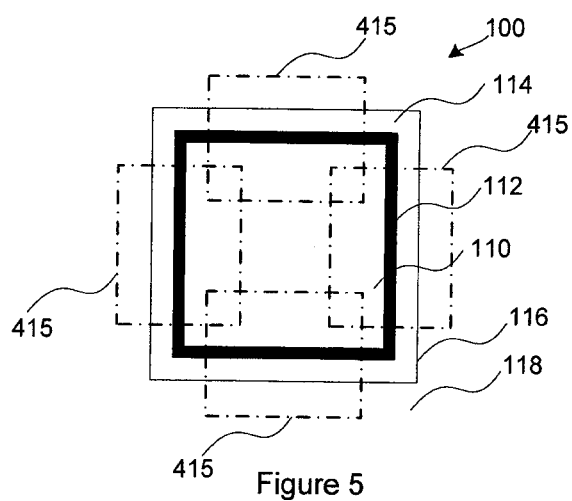
FIG. 5 depicts a multiple zone interconnection pad of a semiconductor device with a plurality of side regions according to the method of the present invention.

The exemplary embodiment, as shown in FIG. 4, begins with an image 400 that is a representation of the pad 100, and user input that roughly defines an innermost zone, for coarse location step 205. Alternatively a single-zone shape registration tool, such as PATMAX® by Cognex Corporation can be used to initially define a rough description of the inner zone. The image 400 is divided into side regions at step 410. FIG. 5 depicts the pad 100 and a plurality of side regions 415. A side region is a portion of the pad 100 that will likely have features associated with zone boundaries having similar orientation. For example, the zone boundary between an inner zone 110 and a central zone 112 can be described as a line segment within side region 415. Similarly, the zone boundary between the central zone 112 and the outer zone 114, and the zone boundary between the outer zone 114 and the device background 118 at the pad border 116, can be described as a line segment within side region 415. One side region is derived for each "side" of the pad, e.g., a rectangular shaped pad will have four side regions 415 as shown in FIG. 5.

A zone boundary in the pad 100 having multiple zones will appear as a line segment in a side region 415. One skilled in the art will appreciate the numerous methods of extracting line segments from an image using machine vision. The exemplary embodiment extracts line segments to find side features 720 in a side region 415 using a series of caliper vision tools. This method is illustrative, and shall not be considered limiting in view of the appended claims.

Starting with a first side region, a plurality of caliper vision tools is applied to the first side region. A caliper vision tool, for example, as provided by Cognex Corporation, is commonly known to one of ordinary skill in the art of machine vision, to locate and measure precise characteristics of edge features in an image. A caliper window, or region of interest, is provided to the tool as a two-dimensional image. The tool then projects the image into a one-dimensional image—a process that can be likened to collapsing the entire window into a single line. The tool applies an edge filter to the one-dimensional image returning the location, polarity, and contrast (or difference in grey level value on either side of the edge) for each edge feature in the caliper window.

In the exemplary embodiment, the side region 415 is divided into seven non-overlapping caliper windows 418, perpendicular to the direction of the pad border 116 and applied to the side region 430. The number of caliper tools applied to each side region can be dynamic, and may be based upon the size of the pad in the image 400. Various parameters can be selected as variables to the caliper tool. Since the images generated by the equipment used in a typical probe mark inspection apparatus 300 are high resolution, with relatively low noise, minimal image smoothing is necessary. In the exemplary embodiment, a conservative contrast threshold of one grey level is used to capture even weak edge features. The position, contrast, polarity and grey level range within 3 pixels (a 3, −3 neighborhood) is retained for each edge feature. The position is a one-dimensional measurement reported by the caliper tool, that is a signed distance along the caliper (perpendicular to the projection) from the edge feature to the center of the caliper window. The grey level range is the range of grey level values of pixels in a 7-pixel neighborhood centered at the edge feature in the normalized caliper projection image, wherein the average pixel intensity of the projected pixels is represented along each projection.

Figure 6:
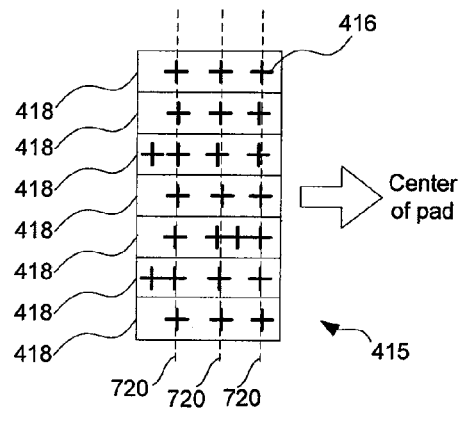
FIG. 6 depicts the features extracted from an image in an exemplary embodiment of the present invention.

The output of the step of applying calipers to a side region 430 is unit features 416 representing edge features in each caliper window 418, that are next combined into clusters 440. FIG. 6 represents a side region 415 and a plurality of caliper windows 418, each caliper window 418 having unit features 416 (represented as "+" signs). Note that the unit features 416 shown in the drawings are, for clarity, not representative of the quantity of unit features 416 that may be found in a typical image. Because the feature detection parameters are set so low, many extra features are detected. Using the method of the present invention herein, the extra features are effectively culled, or removed.

To combine unit features into clusters, step 440 of FIG. 4, the unit features 416 from all seven caliper windows form a single list of unit features sorted in order of their one-dimensional position relative to the center of the seven caliper windows within the side region 415. Each unit feature in the list is compared to its adjacent unit feature in the list to identify compatible neighbors. A pair of unit features is deemed compatible neighbors if they reside within a positional tolerance, exhibit the same polarity (i.e., both are bright-to-dark or dark-to-bright), and express similar changes in contrast. In the exemplary embodiment, a positional tolerance of 2 pixels is used, and similar contrast is found if the ratio of contrast (smaller/larger) is at least 0.6.

For each group of compatible neighbors, a representative position can be expressed as an average, (i.e., mean, or median) position of the group. A representative grey scale range can be expressed as the mean, or median value of the left end of the range of the group of compatible neighbors, and the mean, or median value of the right end of the range of the group of compatible neighbors. Note that a particular unit feature may appear in more than one group, e.g., in groups represented by its left neighbors, in a group represented by itself, and in groups represented by its right neighbors.

Each group of compatible neighbors can be further screened to ensure that a minimum number of unit features are present (to distinguish a group of compatible neighbors associated with noise, or a feature in the image 400 that is not associated with a pad zone). The minimum number of unit features threshold is based on the number of caliper windows 418 in a side region 415. For example, the exemplary embodiment uses a threshold defined as the number of unit features in a group of compatible neighbors plus one must be greater than one-half the number of caliper windows 418. Groups of compatible neighbors that do not meet this threshold are excluded from further consideration.

A non-maxima suppression (NMS) can be performed on the remaining groups of compatible neighbors in order to further define the group of compatible neighbors into clusters. For each side region 415, the unit features are sorted in ascending order of the one-dimensional position. In each side region 415, each unit feature 416 is processed in the following manner. All unit features having a position within a range centered at the position of the unit feature under analysis are identified as a group of unit features. The range in the exemplary embodiment uses 4 pixels (i.e., 2 pixels on either side of the position of the unit feature under analysis). A span is computed for the group of unit features, the span defined as the distance between the two unit features in the group of unit features that are furthest apart. If there are two or more unit features in the group (i.e., there is one or more unit features within the range of the unit feature under analysis), the span is the distance between the two unit features that are furthest apart, though not less than 0.001. If the unit feature under analysis is the only unit feature in the group, the span is set to the value of the range, e.g., four pixels in the exemplary embodiment. Next, a density computation can be made as the total number of unit features in the group divided by the span value. Thus, each unit feature can have an associated density computation once each unit feature is processed.

To continue NMS, in each side region 415, each unit feature is sorted in descending order by density, tagged as "untested." Starting with the unit feature with the highest associated density, a test is applied to each unit feature in the sorted list to accept or reject the unit feature. The unit feature under test is rejected if there was any other unit feature within the previously defined range that also resided in the range of any unit feature in the sorted list that is tested, and accepted. The unit feature is accepted if there was not a unit feature in the previously defined range that resided in the range of any tested unit feature that has since been accepted. The groups of compatible neighbors associated with the rejected unit features are suppressed from further consideration. The remaining groups of compatible neighbors are then considered to be clusters of unit features for further processing.

The clusters of unit features are next generated as a side feature 720 in the side region 450. The clusters are subjected to a consistency check to eliminate clusters composed of spurious features that may originate from noise or non-pad zone features (which is highly likely given the low threshold parameters in the caliper tool to identify edge candidates). For each cluster, gradient direction is examined along a line parallel to the side region 415 and passing through the one-dimensional position of that cluster to determine if a cluster represents a side feature 720 associated with a zone of the pad in the image 400. The exemplary embodiment uses a Sobel kernel for the estimation of gradient direction, requiring at least 60% of the pixels to be within 30 degrees of the expected direction. Each line segment comprised of verified clusters having a consistent gradient direction are considered to be a side feature 720 of step 450, each side feature 720 having the polarity of the cluster to which it is associated.

Figure 7:
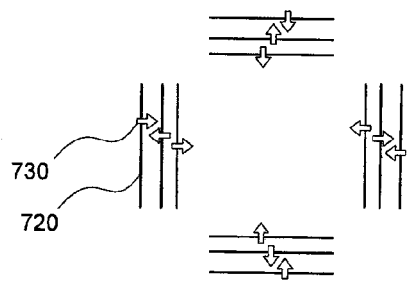
FIG. 7 depicts the combined features extracted from an image in an exemplary embodiment of the present invention.

Referring to FIG. 4, at step 460, a test is applied to determine if all side regions 415 have been analyzed. If not, steps 430-450 are repeated for the next side region, as described by step 470. Once all side features 720 have been identified 480, feature extraction 210 is complete, as shown in FIG. 7.

Figure 8A:
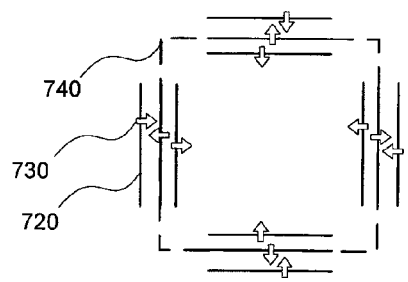
FIG. 8a depicts a first exemplary zone candidate proposed from combined features extracted from an image in an exemplary embodiment of the present invention.
Figure 8B:
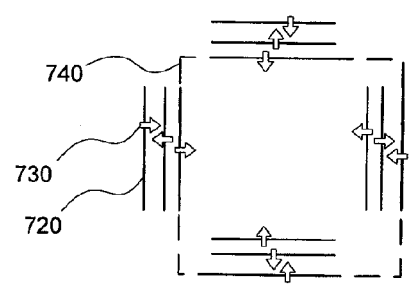
FIG. 8b depicts a second exemplary zone candidate proposed from combined features extracted from an image in an exemplary embodiment of the present invention.

Hypothesis generation 220 takes the side features 720 in the image 480, each side feature having a polarity 730 (shown in FIG. 7 as an arrow indicating the polarity as "dark" to "light") and returns a number of pad geometry hypotheses, each consisting of a number of substantially concentric and non-intersecting zone candidates 740. FIGS. 8a and 8b demonstrate two possible zone candidates 740 that can be derived from the side features 720 and the polarities 730 of the image 480. Zone candidates 740, or combinations of a side feature 720 from each side region 415, can be identified through an exhaustive search over all possible combinations of side features 720, or more efficient methods can be employed.

A zone candidate 740 is removed from consideration if it is composed of any two side features 720 that fail to have the same polarity 730 (both bright-to-dark or dark-to-bright, measured in the direction from the center of the pad through the side feature 720 toward the pad boundary 116). Additional tests can be applied to remove further zone candidates 740 from consideration. For example, an acceptance threshold can be applied to a contrast ratio at the side features 720 by determining a contrast value of each side feature in the zone candidate 740, and calculating a ratio of the contrast to the contrast of adjacent and facing side features in the zone candidate 740. In the exemplary embodiment, zone candidates 740 having adjacent sides with contrast ratios in the range of 0.2 to 5.0, and facing sides with contrast ratios in the range 0.4 to 2.5 are not excluded from further consideration.

Another test can be applied to remove further zone candidates 740 from further consideration by examining the consistency of the grey level range on either side of each side feature 720 in the zone candidate 740. If the grey level range of a side feature 720 of a zone candidate 740 is not similar, within a certain tolerance, to the grey level range of a side feature 720 of an adjacent side feature in the combination, the zone candidate 740 is removed from further consideration. For example, a grey level range for each side feature 720 can be defined as the union of the range of grey level values in a seven pixel neighborhood centered at each unit feature comprising the side feature 720 (i.e., the grey level range in an area comprising three pixels on each side of the unit feature). Consistency in the grey level range between opposing side features 720 can be determined if the upper 80% of the grey level range overlaps in the opposing pair. Similarly, consistency in the grey level range between adjacent side features 720 can be determined if the upper 90% of the grey level range overlaps in the adjacent pair.

An exhaustive search over all possible combinations of side features 720 can be performed to identify zone candidates 740. Alternatively, an efficient method of identifying zone candidates can be performed by avoiding examination of combinations that are expected to fail according to the combinations already examined. For example, if any two side feature 720 combinations are removed from consideration, any further combination using the two side features 720 already removed from consideration are also removed from consideration. Since only valid combinations are returned as zone candidates 740, a full exhaustive search is unnecessary, and therefore, an efficient zone candidate identification is equally effective, but faster.

Figure 9:
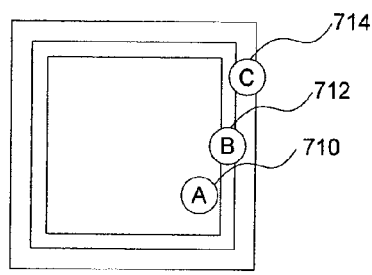
FIG. 9 depicts the multiple zones of a multiple zone interconnection pad of a semiconductor device.

Hypotheses are composed once valid zone candidates 740 are identified, i.e., valid combinations of a side features 720 from each side region 415. A hypothesis is a combination of zone candidates that can describe a pad geometry, as shown in FIG. 9, where a hypothesis is the combination of zone candidates 740 to form zone "A" 710, zone "B" 712, and zone "C" 714. Zones forming a valid hypothesis must not cross each other, must be substantially concentric, and must satisfy certain grey level requirements. The exemplary embodiment requires the centers of each zone to be within three pixels of each zone in the hypothesis. The exemplary embodiment applies a test to ensure that the zones not cross each other. Further, the exemplary embodiment requires that the median grey level of the outermost zone, e.g., "C" be greater than the median grey level of the device background 118.

An area-based contrast evaluation can be performed on the zones of the hypothetical description to test its validity. The contrast evaluation determines if a zone is distinct from its adjacent zone, or that the zone is distinct from the device background 118. An area based contrast evaluation can be performed by calculating a median grey level for the annulus region of each zone and a median grey level for the device background 118 (note that, when computing pixel intensity values for the device background, the device background is defined to be an annulus region of a specified thickness surrounding the outermost zone. In the exemplary embodiment, this thickness is 5% of the larger dimension of the bounding box of the outermost zone, or at least 5 pixels). For each zone, a contrast difference can be determined between it and its immediate enclosing zone, and a contrast difference can be determined between it and the device background 118. An acceptance threshold can be applied so that each zone has at least one contrast difference that exceeds a minimum grey level threshold. The exemplary embodiment applies an acceptance threshold for contrast difference to be 10 for an 8-bit image depth. Referring to FIG. 9, the following inequality represents the area based contrast evaluation of the exemplary embodiment, where the variables A, B, C, and D represent the median grey level of zones A, B, C, and the device background D:

$$\max(|B-C|,|B-D|) \leq \max(0.2 \times \max(|A-D|,|B-D|,|C-D|),10) \quad \text{Equation 1.}$$

All valid combinations of zone candidates are examined, as described in the step of hypothesis generation 220, to return a number of pad geometry hypotheses, each consisting of a number of substantially concentric and non-intersecting zone candidates 740. The hypotheses, which may consist of at least one single, or multiple zone hypothesis, are then passed to the next step of selecting a hypothesis 230.

Hypothesis selection 230 chooses the hypothesis flat best describes the pad geometry among all valid hypotheses generated 220. The selection can be a two-stage process: first, the best hypothesis from those having the same number of zones is selected; then the best from the first stage is selected. Hypothesis selection 230 can be based on a normalized zone contrast C:

$$C = \sum_{n=1}^{N} \frac{c_n}{s_n}. \quad \text{Equation 2}$$

where N is the total number of zones in the hypothesis, $c_n$ is the minimum of an edge-based contrast value and an area based contrast value of zone n, and $s_n$ is the minimum of the grey level standard deviation of zone n and the standard deviation of zone n+1 (note that n+1 refers to the device background 118 if zone n is the outermost zone). Edge based contrast can be defined as the median of the contrast of the zones side features. Area based contrast can be defined as the absolute difference between the median grey level values of the zone and its immediate enclosing zone.

The first stage of hypothesis selection determines the best hypothesis from all having the same number of zones. For example, this stage may yield a one-zone, a two-zone, and a three-zone hypothesis. For any multiple of hypotheses having the same number of zones, the selected hypothesis can be determined to be the hypothesis having the least area encompassed by the outermost zone boundary, i.e., the least overall pad area. If more than one hypothesis has the same least area encompassed by the outmost zone boundary, then the hypothesis having the maximum normalized zone contrast, as defined in Equation 2, is selected.

The second stage of hypothesis selection determines the best hypothesis to describe the pad geometry. If two or more hypotheses share the same outermost zone, then the best hypothesis is the one having the most number of zones. Otherwise, the best hypothesis can be selected as the one having the largest normalized zone contrast, as defined in Equation 2.

The description of the exemplary embodiment has been provided in the context of rectangular device pads, though the method and apparatus of the present invention can be applied to non-rectangular zones and pads. The method and apparatus of the present invention can be applied to any shape pad having substantially concentric multiple zones that have a generally similar shape. For example, side regions 415 of a non-rectangular polygonal shaped pad can be defined as the regions containing each segment of the polygon shape. The number of caliper tools can be a function of the length of the side region. Further, the method and apparatus of the present invention can be applied to circular and elliptical shaped pads by implementing a shape detector, such as a circle detector to detect pad zone candidates 740 directly.

The selected hypothesis from step 230 is returned as the geometric description of regions of the pad 240, that can used be in the inspection step 250 to perform a probe mark inspection of the device pad 100.

Figure 10:
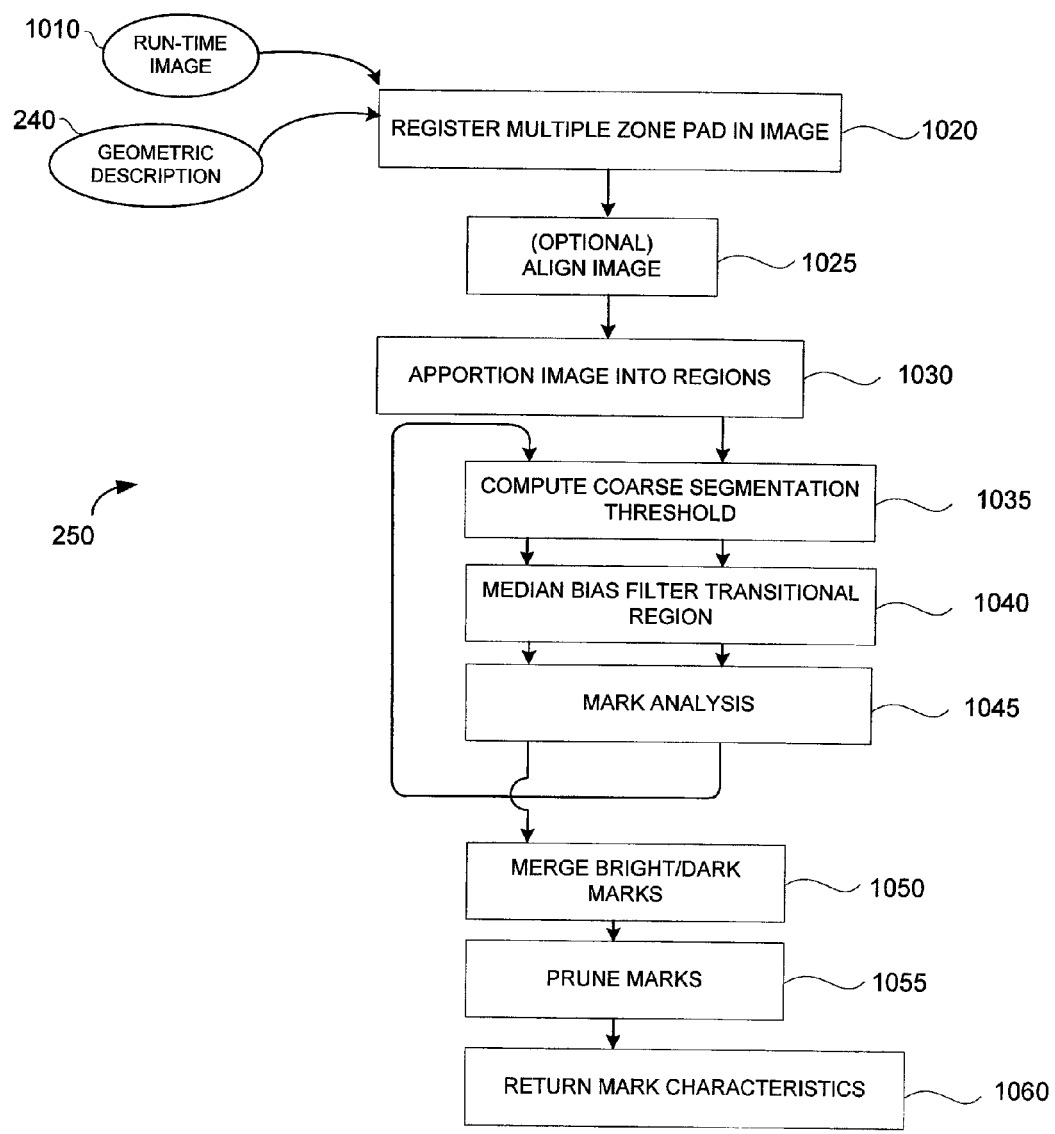
FIG. 10 is a flowchart of the method of inspecting a multiple zone pad.
Figure 11A:
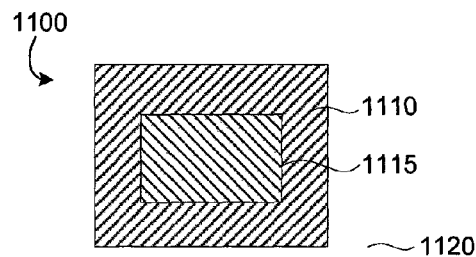
FIG. 11a-d depict the several regions of an image of a pad inspected using the method of the present invention.
Figure 11B:
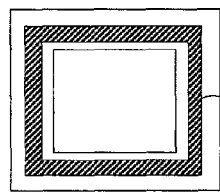
Figure 11C:
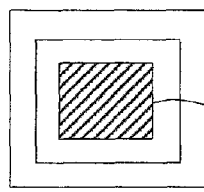
Figure 11D:
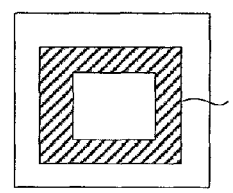

The inspection apparatus 300 can be configured to perform a probe mark inspection of a multiple zone pad during runtime, using the inspection step 250 as shown in FIG. 10. The geometric description of the regions of the pad 240, derived during setup configuration, is used as a model for the runtime inspection. During the inspection step 250, a run-time image of the pad 1010 can be acquired by the inspection apparatus 300.

As shown in FIG. 10, the geometric description of the regions of the pad 240 is registered in the runtime image 1010 at step 1020. A rotation-scale-invariant search can be performed using PATMAX® from Cognex Corporation to register the pad zones in the image. The exemplary embodiment provides for two methods of performing pad registration. Using the first method, each zone can be separately registered, such that each zone can have a different pose (translation, scale, orientation). In this method, the outermost zone is first registered, with the inner zones subsequently registered using a sub-window specified by the outer zone. The advantage of the first method is that it is more tolerant of models having less precision. Using the second method, all zones can be simultaneously registered, using a single, composite model corresponding to the geometric description of regions of the pad 240. The advantage of the second method is that it is more tolerant of images that have indistinct zone boundaries.

Once the zones are registered in the image, it may be necessary to rotate or align the image in order to align the pad with the axes, as shown in optional step 1025. Alignment is performed so that the inspection apparatus 300 can use axis-aligned windows, or sub-regions of the field of view, to characterize rectangular pad zones. Additionally, an axis-aligned image permits the use of masking with less computational requirements at runtime (since the mask can be pre-computed at training time and reused at runtime). In the exemplary embodiment, axis alignment is performed using a preferred method of high accuracy bicubic interpolation if the registered pad is rotated such that corners of the pad which would ordinarily share the same coordinate differ by more than 3 pixels.

The image is next apportioned to the respective regions or zones as defined by the geometric description 240 at step 1030. Apportionment can be performed by labeling each pixel according to the region or zone to which it corresponds. Alternatively, the image can be apportioned by specifying axis-aligned windows corresponding to the zone boundaries if the pad and zone regions are rectilinear. Non-rectilinear pads can be apportioned by specifying a mask that overlays the image according to the geometric description 240.

To distinguish between pixels residing deep within a region or zone from pixels that reside near a zone boundary, the apportionment can be performed to effectively subdivide the zone regions into "associated" regions, and "transitional" regions. Further, the apportionment step can associate regions of the image to that of the "background." The distinction between zone "association" and zone "transition" is important because of the potential for ambiguity in association of pixels near zone boundaries. A pad region can be defined to be associated with a zone by shrinking the region apportioned as a zone at each zone boundary, with the remaining area designated as transitional between zones. For example, as shown in FIG. 11, a two-zone multiple zone pad 1100 has an inner zone 1115, an outer zone 1110, and the background 1120. The apportionment of the multiple zones can be performed as follows. The outer zone 1110 can be reduced in size by two pixels at each boundary to produce an outer associated region 1130 according to FIG. 11b. The inner zone 1115 can be reduced in size by two pixels at each boundary to produce an inner associated region 1140, according to FIG. 11c. The transitional region 1150 will then consist of a four pixel wide annulus region at the transition between the inner zone and the outer zone, according to FIG. 11d.

Referring back to FIG. 10, the following sequence of steps are performed for two possible mark polarities (dark mark, or bright mark): a segmentation threshold can be computed separately for each region of the pad associated with a zone at step 1035; a median bias filter can be performed on the transitional region 1150 at step 1040; and a mark analysis is then performed at step 1045.

A segmentation threshold for the outer zone can be computed separately by computing a threshold for each of the four sides comprising the outer zone, and selecting the minimum (or maximum if the object of inspection is a bright mark) of those four computed threshold values for the overall outer zone threshold. Further, in the exemplary embodiment, the separately-computed outer zone threshold is only applied if the minimum side thickness of the outer zone is less than 3.5 pixels thick. If the minimum side thickness of the outer zone is greater then 4.5 pixels, the overall threshold computed from the entire outer zone is used. If the minimum side thickness is between 3.5 and 4.5 pixels, a bilinear interpolated threshold between the separately computed threshold and the overall threshold computation is applied.

The computation of a coarse segmentation threshold at step 1035 is made on each region associated with a zone, e.g., outer associated region 1130 and inner associated region 1140. The segmentation threshold is computed from a histogram analysis to differentiate between the pad surface and the probe mark. The segmentation threshold can be automatically derived using within-group variance (WGV), commonly known in the art, and described in Computer and Robot Vision, Volume I, by Robert M. Haralick and Linda G. Shapiro, Addison-Wesley (1992), pp. 20-23. An application of WGV will produce a histogram of grey levels on the pad, and choose an optimal threshold for separating the histogram into two distributions such that it minimized the sum of the standard deviations (weighted by the number of contributors) of the two distributions. In the exemplary embodiment, the threshold is clamped to between (possibly) 6 sigma and (definitely) 12 sigma from the mean (the sigma and mean are computed from the middle 50% of the histogram). While the threshold is clamped to be at most 12 sigma, when clamped to be at least 6 sigma, a "fuzzy clamping" is used. The fuzzy clamping is based on a WGV score using the normalized Between Group Variance (BGV). The Between Group Variance is normalized to between 0 and 1 by dividing it by the variance (BGV/Variance). If the WGV score is below 0.78, then we use the "clamp" to ensure that the threshold is at least 6 sigma away (6 sigma is used when looking for marks that appear to be dark on a light background and 8 sigma when looking for marks that appear to be bright on dark backgrounds). If the WGV score is greater than 0.82, then the "clamp" is ignored, and the computed WGV threshold is used. If the WGV score is between 0.78 and 0.82 and if the threshold is outside the clamp range (so that it would be clamped), then the difference between the computed WGV threshold and the sigma-based clamp is computed and multiplied by (1−(0.82−WGV score)/(0.82−0.78)) to determine what fraction of the difference is added to the threshold.

Since the coarse segmentation threshold step 1035 considers both bright and dark probe marks, a tripartite WGV can be used to determine thresholds for bright mark/background, and dark mark/background. The tripartite within-group variance minimizes the same sum as the basic within-group variance algorithm, though operated upon three distributions: bright marks, pad background, and dark marks. The thresholds can be iteratively derived by performing WGV on the upper and lower distributions of the region under analysis. For example, if the region under analysis is the inner associated region 1140, a distribution of greylevel values will likely produce a median greylevel value. Application of WGV on the distribution greater than the median value will yield a threshold t1, and application of WGV on the distribution less than the median will yield a threshold t2. A tripartite WGV can then be performed on the three distributions using the thresholds t1, and t2, to derive an new pair of thresholds defining three distributions (where t1<median<t2). The tripartite WGV can be repeatedly operated until the dark/bright mark thresholds no longer changes.

The median bias filtering step 1040 is performed on the transitional region 1150. Transitional regions 1150 typically will not have instantaneous transitions at zone boundaries, and since the background greylevel is not constant, a uniform greylevel threshold cannot be accurately determined. A conservative approach can thus be applied to detect features of marks in the transitional region 1150 that are extremely apparent.

The greylevel values of the transitional region 1150 can be normalized in the median bias filtering step 1040 by offsetting the pixel values according to a median greylevel value derived for each pad-aligned row/column of the region. The compensation is the difference between the median grey level of that strip and the nominal grey level of the adjacent inner region. Since the pixels are on the image grid, then median pixel values at a particular pixel can be linearly interpolated from the nearby median strips. Also, if a pixel lies in the intersection of a row and a column, its median-biased grey level can be based upon either the row or column depending upon which one makes it closer to the nominal grey level. The transitional region 1150 of FIG. 11d can be separated into a number of pixel-wide strips that corresponds to the width of the transitional region, e.g., a 4-pixel wide transitional region would equate to 16 one-pixel wide strips (4 on the top, 4 on the left, 4 on the bottom, and 4 on the right), while a 5-pixel wide transitional region would correspond to 20 one-pixel wide strips. A median greylevel can be determined in each strip, and each pixel can be compensated by an offset to adjust the median greylevel to that of the inner associated region 1140. For example, if the median greylevel was darker in the inner associated region 1140, then an offset can be determined to increase the median greylevel of each row/column by adding the intensity of each pixel in the strip by the offset.

The use of the term "median" does not necessarily imply a 50% median; it may refer to the 75 percentile or 25 percentile of the cumulative histogram, depending upon whether the object is an analysis of "dark" marks or of "bright" marks relative to the background. The pixel values are used to compute the median grey level for each strip exclude those near known marks (i.e., marks in the adjacent inner region that touch the adjacent inner region boundary). If an insufficient number of pixels remain to accurately compute the median (e.g., less than 25% of the pixels), then the median-bias filtering step for the particular row/column may be skipped.

Figure 12:
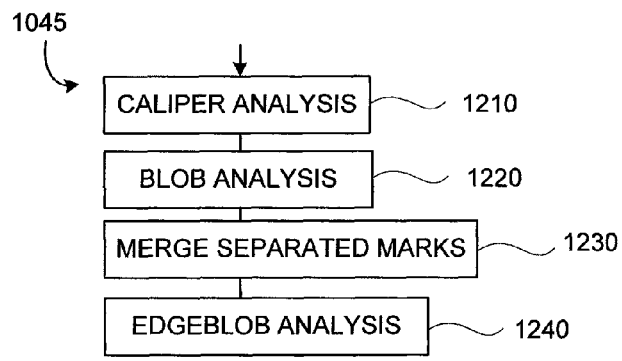
FIG. 12 is a flowchart of the analysis step of the method of inspecting a multiple zone pad.

The mark analysis step 1045 is further described in FIG. 12. If a region under analysis has a width of only one pixel, a caliper, a vision tool commonly known in the art to detect edge features in the pixel strip, can be used to detect edge features, The caliper analysis, as shown in step 1210, can force the pixel intensity to 0 or 100% between the edges of alternating polarity. For example, when a side of the outer zone is only one pixel thick, an edge-based caliper tool, rather than grey level thresholding, can be used to detect defects: the caliper is applied to detect opposite polarity edges. The grey levels between the opposite polarity edges are set to be 0 or 255 (depending upon whether the object of inspection is dark or bright marks). In this analysis of one-pixel width regions, the contrast threshold used for calipers in the exemplary embodiment is a function of the mean grey level, e.g., mean-Greylevel/8.

A blob analysis 1220 is performed on each region using the coarse segmentation threshold of step 1035. In the exemplary embodiment, a blob (connectivity) analysis on the transition and associated region is run together using the segmentation threshold of the associated region. The blob analysis is performed on image processed regions, such as median bias filtering step 1040 and the caliper analysis step 1210, if applicable. A minimum blob size threshold can be employed to filter small surface imperfections that result in "freckles" in the run-time image 1010, though such a minimum blob size threshold may have to be dynamically set depending upon the size of the region under analysis (such as the outer zone region). For example, if a region is very thin, a probe mark may reside in only a portion of the region, which may not exceed a minimum blob size threshold. Consequently, the minimum blob size can be determined to be:

$$\text{minBlobArea} = \min(\text{minBlobArea}, \text{region\_thickness} * \text{sqrt}(\text{minBlobArea})) \quad \text{Equation 3.}$$

Figure 13:
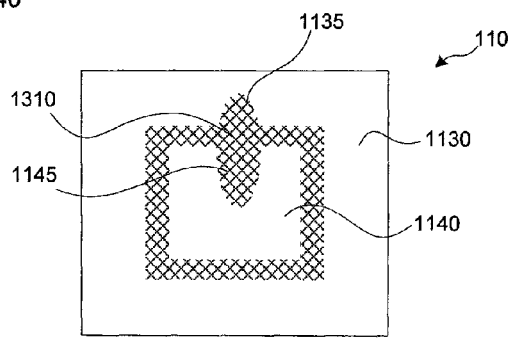
FIG. 13 depicts a probe mark feature separated and merged in the method of the present invention.

Since blob analysis is performed on separate regions at blob analysis step 1220, it can be expected that marks that overlap multiple zones will induce multiple blobs. FIG. 13 shows a run-time image 110 having a inner associated region 1140 with an inner mark feature 1145, and an outer associated region 1130, with an outer mark feature 1135. Separated marks can be merged at step 1230 by locating corresponding boundary points between the inner mark feature 1145 and the outer mark feature 1135. Matching pairs of boundary coordinates are located, and an uninterrupted sequence of blob boundary points between subsequent matching pairs are computed, as shown in FIG. 13 as the merged mark feature 1310.

An edgeblob analysis step 1240 can be performed to refine the mark characteristics using a combination of binary image (blob) analysis with greyscale edge data analysis, as disclosed in U.S. patent application Ser. No. 09/708,431 entitled "Object and Feature Detector System and Method" and U.S. patent application Ser. No. 10/032,168, entitled "Probe Mark Inspection Method and Apparatus," both incorporated herein by reference.

Referring back to FIG. 10, once steps 1035 through 1045 are performed for both bright and dark marks, the results are merged at step 1050. Any pair of marks are merged if the pair contains regions of opposite polarity (bright/dark), and the minimum distance between those regions is within a certain threshold, for example, 8 pixels. Optionally, merging step 1050 can be skipped if there is a sufficiently thick channel of "non-bright/non-dark" pixels between the two regions (i.e., pixels having grey levels between the dark threshold and the bright threshold). The channel thickness threshold in the exemplary embodiment is clamped to between 3 and 6 pixels, and is otherwise expressed as 60% of the smaller of the two largest bounding box dimensions (width or height) of the two marks.

A pruning step 1055 can be performed to remove from further consideration features that do not exceed a minimum size threshold. For example, surface aberrations of the pad may appear as freckles can be distinguished from actual probe mark features since the computed area of the surface aberration, or freckle, will be substantially less than a probe mark.

The result of the inspection step 250 is a probe mark inspection result, such as a report of a detected probe mark characteristic, such as data in the form of a blob scene description of a detected probe mark, including topological and geometric features, that can be returned at step 1060.

While the invention has been described with reference to the certain illustrated embodiments, the words which have been used herein are words of description, rather than words of limitation. Changes may be made, within the purview of the appended claims, without departing from the scope and sprit of the invention in its aspects. Although the invention has been described herein with reference to particular structures, acts, and materials, the invention is not to be limited to the particulars disclosed, but rather extends to all equivalent structures, acts, and materials, such as are within the scope of the appended claims.

We claim:

1. A machine vision method of inspecting a semiconductor interconnection pad, the method comprising:
   acquiring an image of the pad, the pad having a multiple zone pattern;
   automatically deriving a multiple zone geometric description of the multiple zone pattern using the image, wherein the step of automatically deriving comprises:
   extracting a plurality of features from the image;
   generating a plurality of hypothetical geometric descriptions using the features; and
   selecting the multiple zone geometric description from the plurality of hypothetical geometric descriptions, including:
   validating at least one of the plurality of hypothetical descriptions using an area-based contrast evaluation to provide validated hypothetical descriptions; and selecting at least one validated hypothetical description using a maximum number of zones to provide a multiple zone geometric description; and using the multiple zone geometric description in a machine vision inspection of the pad.

2. The method of claim 1 wherein the step of generating a plurality of hypothetical geometric descriptions using the features comprises an acceptance test using a contrast value of the features.

3. The method of claim 1 wherein the step of generating a plurality of hypothetical geometric descriptions using the features comprises an acceptance test using a grey level range of the features.

4. The method of claim 1 wherein the features include at least one of a side feature, an edge feature, a noise feature, a surface defect feature, a feature not associated with boundaries of the multiple zone pattern, a corner boundary of the multiple zone pattern and a side boundary of the multiple zone pattern.

5. The method of claim 1 further comprising the step of comparing at least one of the features to at least one adjacent feature to determine whether the at least one feature is compatible with the at least one adjacent feature.

6. A method for inspecting a semiconductor interconnection pad using a machine vision system, the method comprising:

acquiring an image of the pad, the pad having a multiple zone pattern;

automatically deriving a multiple zone geometric description of the multiple zone pattern using the image, wherein the step of automatically deriving comprises:

extracting at least one zone boundary from a plurality of zone boundaries identified on the image of the multiple zone pattern;

extracting a plurality of features from the at least one zone boundary identified on the image;

generating a plurality of hypothetical geometric descriptions using the features; and selecting the multiple zone geometric description from the plurality of hypothetical geometric descriptions, including:

validating at least one of the plurality of hypothetical descriptions using an area-based contrast evaluation to provide validated hypothetical descriptions; and selecting at least one validated hypothetical description to provide a multiple zone geometric description; and using the multiple zone geometric description in a machine vision inspection of the pad.

7. The method of claim 6 wherein the step of generating a plurality of hypothetical descriptions using the features comprises an acceptance test using a contrast value of the features.

8. The method of claim 6 wherein the step of generating a plurality of hypothetical descriptions using the features comprises an acceptance test using a grey level range of the features.

9. The method of claim 6 wherein the features include at least one of a side feature, an edge feature, a noise feature, a surface defect feature, a feature not associated with boundaries of the multiple zone pattern, a corner boundary of the multiple zone pattern and a side boundary of the multiple zone pattern.

10. An apparatus for inspecting a semiconductor interconnection pad comprising:

means for acquiring an image of the pad, the pad having a multiple zone pattern;

means for automatically deriving a multiple zone geometric description of the multiple zone pattern using the image, wherein the means for automatically deriving comprises:

means for extracting a plurality of features from the image;

means for generating a plurality of hypothetical geometric descriptions using the features; and means for selecting the multiple zone geometric description from the plurality of hypothetical geometric descriptions, including:

means for validating at least one of the plurality of hypothetical descriptions using an area-based contrast evaluation to provide validated hypothetical descriptions; and means for selecting at least one validated hypothetical description using a maximum number of zones to provide a multiple zone geometric description; and means for using the multiple zone geometric description in a machine vision inspection of the pad.

11. The apparatus of claim 10 wherein the means for generating a plurality of hypothetical geometric descriptions using the features comprises an acceptance test using a contrast value of the features.

12. The apparatus of claim 10 wherein the means for generating a plurality of hypothetical geometric descriptions using the features comprises an acceptance test using a grey level range of the features.

13. The apparatus of claim 10 wherein the features include at least one of a side feature, an edge feature, a noise feature, a surface defect feature, a feature not associated with boundaries of the multiple zone pattern, a corner boundary of the multiple zone pattern and a side boundary of the multiple zone pattern.

14. The apparatus of claim 10 further comprising means for comparing at least one feature to at least one adjacent feature to determine whether the at least one feature is compatible with the at least one adjacent feature.

* * * * *